United States Patent [19]

Girgis et al.

[11] Patent Number: 4,762,792

[45] Date of Patent: Aug. 9, 1988

[54] CHOLESTEROL-RICH FRACTION USEFUL IN CULTURE MEDIA AND PROCESS OF PRODUCING SAME

[75] Inventors: Makram M. Girgis, Bradley; David E. Jackson, Bourbonnais; Gerald L. Kruse, Herscher, all of Ill.; Frank J. Mannuzza, Burlington, Mass.; Joseph G. Montalto, Bradley, Ill.

[73] Assignee: Miles Inc., Elkhart, Ind.

[21] Appl. No.: 923,850

[22] Filed: Oct. 28, 1986

Related U.S. Application Data

[63] Continuation-in-part of Ser. No. 732,856, May 10, 1985, abandoned.

[51] Int. Cl.$^4$ ............................................. C12N 1/38
[52] U.S. Cl. ................................. 435/244; 435/243; 435/253; 435/254; 435/240.3; 424/101; 260/397.2; 260/397.25
[58] Field of Search ............... 435/253, 254, 240, 241, 435/243, 244; 424/101; 260/397.2, 397.25

[56] References Cited

U.S. PATENT DOCUMENTS 4,582,807  4/1986  Veeraraghavan ................... 435/253

*Primary Examiner*—Sam Rosen
*Attorney, Agent, or Firm*—Louis E. Davidson

[57] ABSTRACT

A process is provided for isolating and purifying a cholesterol-rich fraction from mammalian blood plasma or serum. The resulting cholesterol-rich fraction is useful as a growth medium ingredient.

12 Claims, No Drawings

4,762,792

CHOLESTEROL-RICH FRACTION USEFUL IN CULTURE MEDIA AND PROCESS OF PRODUCING SAME

This is a continuation-in-part of U.S. patent application Ser. No. 732,856, filed May 10, 1985, now abandoned.

BACKGROUND AND PRIOR ART

This invention relates to the isolation and purification of a cholesterol-rich fraction from mammalian blood plasma or serum which is useful as a growth medium ingredient.

It is known that cholesterol and cholesterol-containing fractions obtained from bovine serum are useful to promote the growth of various organisms. J. Bacteriol., Vol. 135, pp. 818–827 (1978) describes the use of a cholesterol-containing bovine serum fraction in the growth of *Mycoplasma pneumoniae* and *Mycoplasma arthritidis*. J. Gen. Microbiology, Vol. 116, pp. 539–543 (1980) describes the use of USP cholesterol in the growth of *Treponema hyodysenteriae*. U.S. Pat. No. 4,290,774 describes the production of a specific cholesterol-rich fraction from mammalian plasma or serum by an overall process which involves the step of treatment with an alkaline carbonate and an alkaline earth salt. Zeit. Klin. Chem. 6(3), pp. 186–190 (1968) describes the removal of certain lipoproteins from human serum by use of colloidal silicic acid. None of the above prior art discloses or suggests the specific process of the present application or the specific cholesterol-rich fraction produced thereby which is useful as a growth medium ingredient.

SUMMARY OF THE INVENTION

In accordance with the present invention, a process is provided for isolating and purifying a cholesterol-rich fraction from mammalian blood plasma or serum or fraction thereof containing cholesterol which comprises the steps of:

(a) contacting a liquid cholesterol-containing plasma or serum or fraction thereof with a silica adsorbent to adsorb the cholesterol-rich fraction;

(b) separating the adsorbed cholesterol-rich fraction from the remaining liquid plasma or serum;

(c) freezing and thawing the adsorbed cholesterol-rich fraction;

(d) eluting the adsorbed cholesterol-rich fraction at a pH from 9.0 to 11.5;

(e) either before or after step (f) and prior to step (g) adjusting the pH of the cholesterol-rich solution to a value in the range from 11.0 to 13.0;

(f) concentrating the cholesterol-rich solution by ultrafiltration;

(g) dialyzing the concentrated cholesterol-rich solution sequentially against sodium carbonate and water;

(h) further concentrating the dialyzed cholesterol-rich solution by ultrafiltration;

(i) adjusting the pH of the concentrated cholesterol-rich solution to a value in the range from 7.0 to 11.0;

(j) heating the concentrated cholesterol-rich solution at 50° to 100° C. for 30 minutes to 24 hours; and (k) recovering therefrom a purified cholesterol-rich fraction.

The cholesterol-rich fraction produced by this process is a new material useful as a growth medium ingredient.

DESCRIPTION OF THE INVENTION

The starting material for use in the present invention can be any mammalian blood plasma or serum fraction containing cholesterol. Suitable starting materials can be bovine, horse, sheep, pig or human plasma or serum or fraction thereof that contains cholesterol, such as fibrinogen-poor plasma, Cohn Fraction I supernatant, an ammonium sulfate supernatant rich in lipoprotein and the like. The preferred starting material is bovine serum or bovine plasma. If the starting material is serum, it is preferred to add a soluble salt, such as sodium citrate, to an ionic strength of 0.25 to 1.0. Other suitable salts include sodium chloride, sodium phosphate, potassium phosphate, ammonium sulfate and sodium sulfate. The addition of a soluble salt to the above concentration will increase the amount of cholesterol-rich fraction adsorbed in the subsequent silica adsorption step. Bovine or human plasma, for example, is normally collected by a method which includes addition of citrate as an anti-coagulant. This salt concentration is usually sufficient for the adsorption step and no additional salt is needed.

The plasma or serum starting material is maintained at a temperature of from 0° C. to 50°, preferably from 20° C. to 25° C. The pH is adjusted to a range of from 5.5 to 9.0, preferably from 7.0 to 8.0.

The silica adsorbent useful in this invention does not have a critical composition. Appropriate silica materials are the microfine silica available under the trademark Cabosil from Cabot Corporation and the powdered silica available under the trademark Aerosil 380 from Cary Company. The silica is added to the liquid plasma or serum in an amount of 1 to 50 g/l., preferably from 10 to 20 g/l. The silica suspension in the liquid plasma or serum is then mixed for about 3 to 4 hours. It is preferred to add to the silica suspension about 10 g/l of a polyethylene glycol having a nominal molecular weight of about 3350 daltons. A suitable material is Union Carbide Corporation Carbowax PEG 3350. The polyethylene glycol aids in the subsequent separation of the silica.

The silica containing adsorbed cholesterol-rich fraction is then separated from the remaining liquid plasma or serum preferably by centrifugation, and the liquid phase is discarded. The silica paste is then frozen at −20° C. and held at this temperature for at least one week and preferably two weeks. The frozen paste is then thawed to room temperature (about 20°–25° C.) for 24 to 48 hours until no visible ice crystals are present. Any liquid that is expressed from the thawed paste is discarded.

The silica paste is washed to remove any undesirable proteins. This is accomplished by suspending the paste in an aqueous salt solution containing about 0.15M sodium chloride. Other useful salts are sodium acetate and sodium phosphate. The salt solution is used in an amount about 2 liters for each kilogram of the paste. The paste is separated from the liquid. This washing procedure using a salt solution is preferably repeated at least two times to remove occluded proteins.

The washed paste is suspended in about 2 liters of deionized or distilled water per kilogram of paste, and the pH is adjusted to 9.0 to 11.5, preferably 10.4 to 10.6, by the addition of appropriate amounts of sodium hydroxide or hydrochloric acid. The suspension is stirred for about 2 hours during which time the pH is maintained at the desired level by periodic additions of the above alkaline or acid material. This treatment elutes the desired cholesterol-rich fraction from the silica. The suspension is then allowed to settle for 12 to 24 hours, preferably 12-18 hours. The supernatant containing the cholesterol-rich fraction is siphoned off for further treatment. It is preferred to use only this first elution for production of the desired cholesterol-rich fraction product. However, it is possible to repeat the above alkaline suspension, elution, stirring and settling steps two more times and pool the supernatants from the second and third elutions with the first elution material. The silica is discarded.

The cholesterol-rich solution is clarified by filtration and centrifugation to remove any traces of silica and then preferably frozen at −20° C. and stored at that temperature for 48-72 hours. The frozen material is then thawed at room temperature for at least 24-48 hours until no visible ice crystals are present. The resulting liquid product is clarified by centrifugation and any solid material is discarded. This freeze-thaw cycle assists in removal of silica which otherwise interferes with subsequent processing steps. The clarified liquid is then concentrated to 15 to 50 percent, preferably 20 to 25 percent, of its initial volume, by ultrafiltration techniques.

The concentrated cholesterol-rich solution is then dialyzed against an alkaline material, such as aqueous sodium carbonate, to further remove silica. In order to improve the effectiveness of this dialysis step, it is desirable for the cholesterol-rich solution to be at pH 11.0 to 13.0, preferably pH 12.0 The pH can be adjusted to this value by alkaline addition. This can take place just prior to the dialysis step, but it is preferred for operating convenience to adjust the pH to this value before the cholesterol-rich solution is subjected to the above-discussed ultrafiltration concentration step.

In the dialysis step, the cholesterol-rich solution is dialyzed against 6-7 volumes of 0.01-0.3M sodium carbonate to remove silica followed by dialysis against 6-7 volumes of deionized water to remove the sodium carbonate. The resulting solution is then concentrated by ultrafiltration to its volume prior to dialysis.

The pH of the concentrated cholesterol-rich solution is then adjusted to a value in the range from 7.0 to 11.0, preferably pH 8.6.

The concentrated cholesterol-rich solution is heated to 50° to 100° C., preferably 80° C., for 30 minutes to 24 hours, preferably 30 minutes to 5 hours, in order to increase the storage stability of the cholesterol-rich fraction. The solution is then cooled to about 30° C. It is convenient for handling purposes that the desired product contain about 0.50 to 30 mg./ml, preferably 10 to 20 mg./ml, of cholesterol. It is preferred to analyze the above cooled product for cholesterol using known techniques and to dilute the product with deionized water to the desired concentration.

While it is not necessary in the process for production of the cholesterol-rich fraction, it is convenient that the product contain about 8.5 g/l sodium chloride and have a pH adjusted to 7.7-7.9 so that it is generally compatible with media employed for cell culture. The product is then sterile filtered to recover a purified cholesterol-rich fraction. This product is not pure cholesterol, but it is mixed with minor amounts of unidentified materials which passed through the production process. This resulting mixture has been found to be quite useful as a growth medium ingredient.

The invention will be further described in the following Examples.

EXAMPLE 1

Fresh bovine serum was brought to a temperature of 20°-25° C. and 14.7 g/l of sodium citrate (serum ionic strength of 0.5) was added. The resulting solution was agitated for 30 minutes, and the pH was adjusted to 7.0 by addition of an appropriate amount of 1N sodium hydroxide. Finely-divided silica was added in an amount of 10 g/l and the resulting slurry was agitated for 3 hours at room temperature. The silica containing adsorbed material was then separated from the liquid phase by centrifugation, and the liquid was discarded. The silica paste was then frozen at −20° C. and stored at that temperature for 2 weeks. The frozen paste was then thawed at room temperature for 48 hours. The expressed liquid was discarded. The silica paste was then suspended in 2 liters of 0.85 percent (weight-/volume basis) aqueous sodium chloride solution (0.146M NaCl) for each kilogram of silica paste. It was mixed gently for 15 minutes and allowed to settle for at least 3 hours. The supernatant liquid was siphoned off and discarded. This washing step was repeated two times. The washed paste was then suspended in 2 liters of deionized water per kilogram of silica paste with agitation at room temperature. The resulting suspension was then carefully warmed to 20°-25° C. The pH was adjusted to 10.5 with addition of 1N sodium hydroxide. The resulting suspension was stirred at room temperature for 2 hours while readjusting pH to 10.5. The stirring was stopped, and the suspension was allowed to settle for 18 hours. The supernatant was removed by siphon and clarified by filtration and centrifugation. The silica was discarded. The clarified solution was then concentrated to 20 percent of its initial volume by ultrafiltration. The pH of the concentrated material was adjusted to 11.2 by addition of 1N sodium hydroxide. The concentrated material was then dialyzed against 6 volumes of 0.01M sodium carbonate at pH 11.2. it was then dialyzed against 6 volumes of deionized water. The cholesterol level of the cholesterol-rich concentrate was analyzed by known techniques and further concentrated by ultrafiltration to a cholesterol level of 1000 mg./dl. (10 mg./ml). The pH was then adjusted to 7.6 by addition of 1N hydrochloric acid, and the resulting solution was heated at 80° C. for 1 hour. The solution was then cooled to room temperature. Sodium chloride was added in an amount of 8.5 g/l and the resulting solution was sterile filtered. The filtered material was then recovered as a purified cholesterol-rich fraction.

The above-prepared cholesterol-rich fraction was added to a known culture medium for *Treponema hyodysenteriae* in an amount of 2.5 volume percent, and the organism was grown therein. The presence of the above-prepared cholesterol-rich fraction doubled the total cell count, increased the viable cell count 100 fold and had a positive effect on cell morphology as compared to growth wherein the above-prepared cholesterol-rich fraction was not present.

EXAMPLE 2

Fresh bovine serum was brought to a temperature of 20°-25° C. and 14.7 g/l of sodium citrate (serum ionic strength of 0.5) was added. The resulting solution was agitated for at least 30 minutes, and the pH was adjusted to 6.9-7.1 by addition of appropriate amount of 1N sodium hydroxide or 1N hydrochloric acid. Finely-divided silica was added in an amount of 10 g/l, and the resulting slurry was agitated for 3-4 hours at room temperature. Polyethylene glycol having nominal molecular weight of 3350 daltons was added in an amount of 10 g/l, and the resulting mixture was agitated for 1 hour at room temperature. The silica containing adsorbed material was then separated from the liquid phase by centrifugation, and the liquid was discarded. The silica paste was then frozen at −20° C. and stored at that temperature for at least 2 weeks. The frozen paste was then thawed at room temperature for 24–48 hours until no visible ice crystals were present. The expressed liquid was discarded. The silica paste was then suspended in 2 liters of 0.85 percent (weight-/volume basis) aqueous sodium chloride solution (0.146M NaCl) for each kilogram of silica paste. It was mixed gently for 15 minutes and allowed to settle for at least 3 hours for adequate sedimentation. The supernatant liquid was siphoned off and discarded. This washing step was repeated at least two times. The washed paste was then suspended in 2 liters deionized water per kilogram of silica paste with agitation at room temperature. The resulting suspension was then carefully warmed to 20°–25° C. The pH was adjusted to 10.5 with addition of 1N sodium hydroxide. The resulting suspension was stirred at room temperature for 2 hours while constantly maintaining pH at 10.4–10.6 by addition of 1N sodium hydroxide or hydrochloric acid. The stirring was stopped, and the suspension was allowed to settle for at least 12 hours. The supernatant was removed by siphon and clarified by filtration and centrifugation. The silica was discarded. The liquid was then frozen at −20° C. and stored at that temperature for 48–72 hours. The frozen material was then thawed at room temperature for 48–72 hours until no visible ice crystals were present. The resulting liquid product was clarified by centrifugation and any solid material was discarded. The pH of the clarified solution was adjusted to 11.9–12.1 by addition of 1N sodium hydroxide. The solution was then concentrated to about 20–25 percent of its initial volume by ultrafiltration using hollow fiber or spiral wound molecular filters having a nominal molecular weight cut-off of 5,000–30,000 daltons. The concentrated material was then dialyzed against 7 volumes of 0.3M sodium carbonate and against 7 volumes of deionized water. The solution was then concentrated by ultrafiltration to its volume prior to dialysis. The pH was then adjusted to 8.6 by addition of 1N hydrochloric acid, and the resulting solution was heated at 80° C. for at least 30 minutes. The solution was then cooled to about 30° C. The cholesterol level of the product was analyzed by known techniques and diluted to a concentration of 10 mg./ml. with deionized water. Sodium chloride in an amount of 8.5 g/l was then added and the pH was adjusted to 7.7–7.9 by addition of 1N sodium hydroxide or hydrochloric acid. The resulting product was then sterile filtered using 0.45 and 0.2 micron microporous filtration media. The filtered material was then recovered as a purified cholesterol-rich fraction.

This product material can be used in the same manner as that described above in Example 1.

What is claimed is:

1. A process for isolating and purifying a cholesterol-rich fraction from mammalian blood plasma or serum or fraction thereof containing cholesterol which comprises the steps of:
   (a) contacting a liquid cholesterol-containing plasma or serum or fraction thereof with a silica adsorbent to adsorb the cholesterol-rich fraction;
   (b) separating the adsorbed cholesterol-rich fraction from the remaining liquid plasma or serum;
   (c) freezing and thawing the adsorbed cholesterol-rich fraction;
   (d) eluting the adsorbed cholesterol-rich fraction at a pH from 9.0 to 11.5;
   (e) either before or after step (f) and prior to step (g) adjusting the pH of the cholesterol-rich solution to a value in the range from 11.0 to 13.0;
   (f) concentrating the cholesterol-rich solution by ultrafiltration;
   (g) dialyzing the concentrated cholesterol-rich solution sequentially against sodium carbonate and water;
   (h) further concentrating the dialyzed cholesterol-rich solution by ultrafiltration;
   (i) adjusting the pH of the concentrated cholesterol-rich solution to a value in the range from 7.0 to 11.0;
   (j) heating the concentrated cholesterol-rich solution at 50° to 100° C. for 30 minutes to 24 hours;
   (k) recovering therefrom a purified cholesterol-rich fraction.

2. A process according to claim 1 employing bovine plasma or bovine serum as the source of cholesterol.

3. A process according to claim 1 wherein between steps (a) and (b) the silica and adsorbed cholesterol-rich fraction are mixed with polyethylene glycol.

4. A process according to claim 1 wherein step (d) is carried out at pH 10.4 to 10.6.

5. A process according to claim 1 wherein step (e) is carried out at pH 12.0.

6. A process according to claim 1 wherein step (i) is carried out at pH 8.6.

7. A process according to claim 1 wherein step (j) is carried out at 80° C. for 30 minutes to 5 hours and the resulting product is adjusted to pH 7.7–7.9.

8. A process according to claim 1 wherein step (f) is carried out to concentrate the eluted cholesterol-rich solution to a volume of 15 to 50 percent of the starting volume.

9. A process according to claim 1 wherein prior to step (k) the cholesterol-rich fraction is adjusted to a cholesterol concentration of 0.50 to 30 mg/ml.

10. A process according to claim 1 wherein after step (d) and before step (f) the cholesterol-rich fraction is subjected to freezing and thawing.

11. A cholesterol-rich fraction obtained by the process of claim 1.

12. A process for isolating and purifying a cholesterol-rich fraction from bovine plasma or serum containing cholesterol which comprises the steps of:
   (a) contacting the liquid bovine serum or plasma with a silica adsorbent to adsorb the cholesterol-rich fraction;
   (b) separating the adsorbed cholesterol-rich fraction from the remaining liquid serum or plasma;
   (c) freezing and thawing the adsorbed cholesterol-rich fraction;
   (d) eluting the adsorbed cholesterol-rich fraction at a pH from 10.4 to 10.6;
   (e) freezing and thawing the eluted cholesterol-rich fraction;
   (f) adjusting the pH of the cholesterol-rich fraction to a value of 12.0;
   (g) concentrating the cholesterol-rich fraction by ultrafiltration to a volume from 15 to 50 percent of the starting volume;

(h) dialyzing the concentrated cholesterol-rich fraction sequentially against sodium carbonate and water;
(i) further concentrating the dialyzed cholesterol-rich fraction by ultrafiltration to the volume it had at the beginning of step (h);
(j) adjusting the pH of the concentrated cholesterol-rich fraction to a value of 8.6;
(k) heating the concentrated cholesterol-rich fraction at 80° C. for 30 minutes to 5 hours;
(l) recovering therefrom a purified cholesterol-rich fraction.

* * * * *